United States Patent [19]

Hesse et al.

[11] Patent Number: 4,924,000
[45] Date of Patent: May 8, 1990

[54] PREPARATION OF ACYLATED IMIDAZOLES

[75] Inventors: Michael Hesse, Ludwigshafen; Wolfgang Hoelderich, Frankenthal; Toni Dockner, Meckenheim; Hermann Koehler, Beindersheim, all of Fed. Rep. of Germany

[73] Assignee: BASF Aktiengesellschaft, Ludwigshafen, Fed. Rep. of Germany

[21] Appl. No.: 321,110

[22] Filed: Mar. 9, 1989

[30] Foreign Application Priority Data

Mar. 11, 1988 [DE] Fed. Rep. of Germany ....... 3808071

[51] Int. Cl.$^5$ .......................................... C07D 233/54
[52] U.S. Cl. .................................................. 548/343
[58] Field of Search .......................................... 548/343

[56] References Cited

FOREIGN PATENT DOCUMENTS 0116205  8/1984  European Pat. Off. .
156644  10/1985  European Pat. Off. .
3228266  2/1984  Fed. Rep. of Germany .

OTHER PUBLICATIONS

S. Iwasaki, Helv. Chim. Acta, 59, 2738 (1976).

Primary Examiner—Richard A. Schwartz
Attorney, Agent, or Firm—Keil & Weinkauf

[57]  ABSTRACT

Acylated imidazoles of the formula

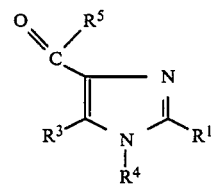

where $R^1$ and $R^3$ are each H, alkyl of from 1 to 12 carbon atoms, alkenyl of from 1 to 12 carbon atoms, aryl, aralkyl or alkylaryl, $R^4$ is H, alkyl of from 1 to 12 carbon atoms, alkenyl of from 1 to 12 carbon atoms, aryl, aralkyl or alkylaryl, and $R^5$ is alkyl of from 1 to 12 carbon atoms, alkenyl of from 1 to 12 carbon atoms, aryl, aralkyl, alkylaryl or carboxyl, are prepared by reacting imidazoles of the formula

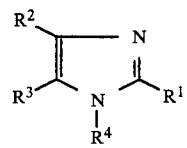

where $R^1$, $R^2$ and $R^3$ are each alkyl of from 1 to 12 carbon atoms, alkenyl of from 1 to 12 carbon atoms, aryl, aralkyl or alkylaryl, at least one of the radicals $R^1$, $R^2$ and $R^3$ being hydrogen, and $R^4$ is H, alkyl of from 1 to 12 carbon atoms, alkenyl of from 1 to 12 carbon atoms, aryl, aralkyl or alkylaryl, with widely used acylating agents of the formula

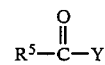

where $R^5$ is as defined above and Y is halide, alkoxy, acyloxy or hydroxyl, in the presence of acidic metal oxides and/or phosphates, preferably in the gas phase.

4 Claims, No Drawings

PREPARATION OF ACYLATED IMIDAZOLES

The present invention relates to a process for preparing acylated imidazoles by direct acylation of appropriate unsubstituted or substituted imidazoles with widely used acylating agents over acidic metal oxides and phosphates.

Heretofore, direct C-acylations of imidazoles in Friedel-Crafts reactions were not known or indeed considered feasible (A. R. Katritzky, C. W. Rees, Comprehensive Heterocyclic Chemistry, Vol. 5, page 402 (1984), Pergamon Press; K. Hofmann, The Chemistry of Heterocyclic Compounds, Vol. 6; Imidazole and its derivatives, Part I, page 49 and page 59 (1953), Interscience Publishers).

For this reason it was necessary to resort to other means, for example the photochemical rearrangement of N-acetylimidazoles (J. L. La Mattina et al., J. Org. Chem. 48 (1983), 897-8), the reaction of 4-formylimidazoles with a Grignard reagent and subsequent oxidation (for example R. Paul et al., J. Med. Chem. 28 (1985), 1704-16) or the hydrogenolysis of a 4-acylamino-5-methylisoxazole (EP 156, 644, Pfizer).

However, these prior art processes are resource intensive and not suitable for industrial application.

We have found, surprisingly, that C-acylated imidazoles of the formula (I)

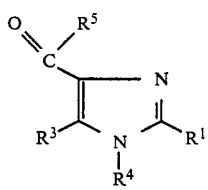

where $R^1$ and $R^3$ are each H, alkyl of from 1 to 12 carbon atoms, alkenyl of from 1 to 12 carbon atoms, aryl, aralkyl or alkylaryl, $R^4$ is H, alkyl of from 1 to 12 carbon atoms, alkenyl of from 1 to 12 carbon atoms, aryl, aralkyl or alkylaryl, and $R^5$ is alkyl of from 1 to 12 carbon atoms, alkenyl of from 1 to 12 carbon atoms, aryl, aralkyl, alkylaryl or carboxyl, are obtained directly, while avoiding the disadvantages of the existing multistage and resource intensive processes on reacting imidazoles of the formula (II)

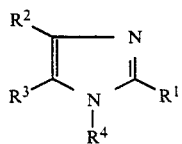

where $R^1$, $R^2$ and $R^3$ are each alkyl of from 1 to 12 carbon atoms, alkenyl of from 1 to 12 carbon atoms, aryl, aralkyl or alkylaryl, at least one of the radicals $R^1$, $R^2$ and $R^3$ being hydrogen, and $R^4$ is H, alkyl of from 1 to 12 carbon atoms, alkenyl of from 1 to 12 carbon atoms, aryl, aralkyl or alkylaryl, with widely used acylating agents of the formula (III)

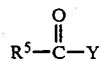

where $R^5$ is as defined above and Y is halide, alkoxy, acyloxy or hydroxyl, in the presence of acidic metal oxides and/or phosphates.

The reaction of 2-methylimidazole with acetic anhydride to give 4-acetyl-2-methylimidazole over a catalyst may be represented for example by the following equation:

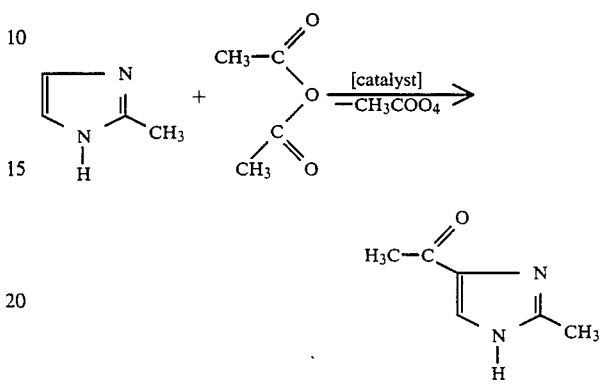

The analogous reaction of 4-methylimidazole gives in the main 5-acetyl-4-methylimidazole, but in addition also 2-acetyl-4-methylimidazole.

Examples of suitable starting materials of the above-mentioned formula (II) for the process according to the invention are imidazole, 2-methylimidazole, 2-ethylimidazole, 2-propylimidazole, 2-isopropylimidazole, 2-decylimidazole, 2-dodecylimidazole, 1-methylimidazole, 4-methylimidazole, 2-ethyl-4-methylimidazole, 4-n-butylimidazole, 2-isopropylimidazole, 2-isopropyl-4-ethylimidazole, 2,4-di-n-butylimidazole, 2-phenylimidazole, 4-phenylimidazole and 4-benzylimidazole.

Examples of acylating agents are acetyl chloride, acetic acid, acetic anhydride, methyl acetate, ethyl acetate, acetamide, propionyl chloride, propionic acid, propionic anhydride, butyryl chloride, butyric acid, butyric anhydride, isobutyric acid, isobutyryl chloride, isobutyric anhydride, crotonic acid, crotonic anhydride, isoprenic acid, valeric acid, valeroyl chloride, caproic acid, caproic ester, pivalic acid, pivaloyl chloride, acrylic acid, methyl acrylate, methacrylic acid, methacrylic esters, methyl 3-pentenoate, methyl 2-pentenoate, methyl 4-pentenoate, sorbic acid, methyl sorbate, benzoic acid, benzoyl chloride, methyl benzoate, o-, m- or p-fluorobenzoic acid, o-, m- or p-fluorobenzoyl chloride, o-, m- or p-chlorobenzoic acid, o-, m- or p-methylbenzoic acid, o-, m- or p-methylbenzoyl chloride, o-, m- or p-methoxybenzoic acid, o-, m- or p-methoxybenzoyl chloride, o-, m- or p-isopropylbenzoic acid, o-, m- or p-isopropylbenzoyl chloride, 2,3-dimethyl-, 2,3-difluoro-, 2,3-dichloro- or 2,3-dimethoxy-benzoic acid or -benzoyl chloride, phenylacetic acid, phenylacetyl chloride, phenylacetic anhydride, cinnamic acid, cinnamoyl chloride, malonic acid, malonic anhydride, phthalic acid, phthalic anhydride, terephthalic acid and terephthaloyl chloride.

Examples of suitable catalysts are acidic metal oxides such as the acidic oxides of elements of main groups II to IV and subgroups III to VI of the periodic table, in particular silicon dioxide in the form of silica gel, diatomaceous earth, quartz, and also titanium dioxide, zirconium dioxide, phosphorus oxides, vanadium pentoxide, niobium oxide, boron trioxide, aluminum oxide, chromium oxides, molybdenum oxides, tungsten oxides, or mixtures thereof. A modification with metals or acids is possible.

It is also possible to use catalysts which have been impregnated with phosphoric acid or boric acid. Phosphoric acid or boric acid is applied to $SiO_2$, $Al_2O_3$ or pumice carriers, for example by impregnating or spraying. A catalyst which contains phosphoric acid can be obtained for example by impregnating $SiO_2$ with $H_3PO_4$ or $NaH_2PO_4$ or $Na_2HPO_4$ solution and subsequent drying or calcination. However, phosphoric acid may also be sprayed together with silica gel in a spray tower; this is followed by drying and usually a calcination. Phosphoric acid may also be sprayed onto the carrier material in an impregnating mill.

Further catalysts for the acylation of imidazoles are phosphates, in particular aluminum phosphates, silicon aluminum phosphates, silicon iron aluminum phosphates, cerium phosphates, zirconium phosphates, boron phosphates, iron phosphates, strontium phosphates and mixtures thereof.

Phosphate catalysts used can be precipitated aluminum phosphates. Such an aluminum phosphate is obtained on dissolving 92 g of diammonium hydrogen phosphate in 700 ml of water and adding 260 g of $Al(NO_3)_3 \times H_2O$ in 700 ml of water dropwise over 2 hours, during which the pH is maintained at pH 8 by the simultaneous addition of 25% strength $NH_3$ solution. The precipitate formed is subsequently stirred for 12 hours, then filtered off with suction and washed. It is dried at 60° C./16 h.

Boron phosphates which are suitable for use as catalysts for the process according to the invention may be prepared for example by mixing and kneading concentrated boric acid or phosphoric acid and subsequent drying and calcination in an inert gas, air or steam atmosphere at from 250° to 650° C., preferably at from 300° to 500° C.

The aluminum phosphate catalysts used for the process according to the invention are aluminum phosphates synthesized in particular under hydrothermal conditions. Suitable aluminum phosphates are for example APO-5, APO-9, APO-11, APO-12, APO-14, APO-21, APO-25, APO-31 and APO-33.

$AlPO_4$-5 (APO-5) can be synthesized by mixing orthophosphoric acid with pseudoboehmite (Catapal SB R) in water to give a homogeneous mixture; tetrapropylammonium hydroxide is added, and the mixture is then reacted in an autoclave at about 150° C. under autogenous pressure for from 20 to 60 hours. The $AlPO_4$ is filtered off, dried at from 100° to 150° C. and calcined at from 450° to 550° C.

$AlPO_4$-9 (APO-9) is synthesized from orthophosphoric acid and pseudoboehmite in an aqueous DABCO solution (1,4-diazabicyclo[2.2.2]octane) at about 200° C. under autogenous pressure in the course of from 200° to 400 hours. If the DABCO solution is replaced by ethylenediamine, APO-12 is obtained.

$AlPO_4$-21 (APO-21) is synthesized from orthophosphoric acid and pseudoboehmite in an aqueous pyrrolidone solution at from 150° to 200° C. under autogenous pressure in the course of from 50 to 200 hours.

In the process according to the invention, it is also possible to use known silicon aluminum phosphates such as SAPO-5, SAPO-11, SAPO-31 and SAPO-34. These compounds are prepared by crystallization from aqueous mixture at from 100° to 250° C. under autogenous pressure in the course of from 2 hours to 2 weeks, the reaction mixture, which is composed of a silicon, aluminum and phosphorus component, being converted in an aqueous organoamine solution.

SAPO-5 is obtained by mixing $SiO_2$ suspended in aqueous tetrapropylammonium hydroxide solution with an aqueous suspension of pseudoboehmite and orthophosphoric acid and subsequent reaction at from 150° to 200° C. under autogenous pressure in a stirred autoclave in the course of from 20 to 200 hours. The powder is filtered off, dried at from 110° to 150° C. and calcined at from 450° to 550° C.

Suitable silicon aluminum phosphates also include ZYT-5, ZYT-6, ZYT-7, ZYT-9, ZYT1-11 and ZYT-12.

To maximize selectivity, conversion and catalyst life, it is advantageous to modify the catalysts.

A possible modifying technique comprises subjecting the material, in molded or unmolded form, to a treatment with acids such as hydrochloric acid, hydrofluoric acid and phosphoric acid and/or steam. An advantageous procedure is to treat the catalysts in powder form with 1 N phosphoric acid at 80° C. for 1 hour. After the treatment the catalyst is washed with water, dried at 110° C./16 h and calcined at 500° C./20 h. Alternatively, the catalysts are treated before or after molding with binders, for example at from 60° to 80° C. with from 3 to 25% strength by weight, in particular from 12 to 20% strength by weight, aqueous hydrochloric acid for from 1 to 3 hours. Thereafter the catalyst thus treated is washed with water, dried and calcined at from 400° to 500° C.

A special embodiment of acid treatment comprises treating the material before it is molded at elevated temperatures with from 0.001 N to 2 N hydrofluoric acid, preferably from 0.05 to 0.5 N hydrofluoric acid, by refluxing for from 0.5 to 5 hours, preferably for from 1 to 3 hours. After the material has been isolated by filtering and washing, it is conveniently dried at from 100° to 160° C. and calcined at from 450° to 600° C. In a preferred embodiment of the acid treatment, the material, after it has been molded with a binder, is treated at an elevated temperature, conveniently at from 50° to 90° C., with from 3 to 25% strength by weight hydrochloric acid, preferably with from 12 to 20% strength by weight hydrochloric acid, for from 1 to 3 hours. Thereafter the material is washed, dried at from 100° to 160° C. and calcined at from 450° to 600° C. A successive treatment with HF and HCl may also be advantageous.

Another procedure comprises modifying the catalysts by applying phosphorus compounds, such as trimethyl phosphate, trimethoxyphosphine, or primary, secondary or tertiary sodium phosphates. The treatment with primary sodium phosphate has proved to be advantageous. In this case, the zeolites are impregnated in extruded, tablet or fluidizable form with aqueous $NaH_2PO_4$ solution, dried at 110° C. and calcined at 500° C.

The catalysts described may as a matter of choice be used in the form of extrudates from 2 to 4 mm, as tablets from 3 to 5 mm in diameter, as chips from 0.1 to 0.5 mm in particle size or as fluidizable material.

The reaction according to the invention is preferably carried out in the gas phase at from 300° to 600° C., in particular at from 400° to 550° C., in a fixed or fluidized bed using a weight hourly space velocity (WHSV) of from 0.1 to 20 $h^{-1}$, in particular of from 0.5 to 5 $h^{-1}$ (g of starting mixture per g of catalyst per hour).

It is also possible to carry out the reaction in the liquid phase (by the suspension, trickle bed or liquid phase procedure) at from 50° to 300° C., in particular at from 100° to 250° C., with a starting material:catalyst weight ratio of from 100:1 to 5:1, preferably from 60:1 to 10:1.

The process may be carried out under atmospheric pressure or, depending on the volatility of the starting compound, under reduced pressure or superatmospheric pressure, preferably continuously.

Sparingly volatile or solid starting materials are used in dissolved form, for example in THF, toluene or petroleum ether solution. In general, the starting material may be diluted with solvents or with inert gases, such as $N_2$, Ar, He or $H_2O$ vapor.

After the reaction, the acylated imidazoles are isolated from the reaction mixture in a conventional manner, for example by distillation; unconverted starting mixture is recycled, if appropriate.

EXAMPLES 1 TO 10

The reaction is carried out in the gas phase under isothermal conditions in a tubular reactor (coil, 0.6 cm in internal diameter, 90 cm in length) for at least 6 hours. The reaction products are separated off in a conventional manner and characterized by GC/MS, NMR and melting point determination. The quantitative determination of the reaction products and the starting materials is done by gas chromatography.

The catalysts used in the application examples below are:

Catalyst A
Commercial $Al_2O_3$ (D 10-10 ®, BASF) in the form of extrudates

Catalyst B Commercial $SiO_2$ (D 11-10 ®, BASF) in the form of extrudates

Catalyst C
Commercial zirconium phosphate $Zr_3(PO_4)_4$ is molded with a molding aid into 2-mm extrudates and dried at 110° C. and calcined at 500° C./16 h.

Catalyst D
Catalyst D is a precipitated boron phosphate prepared by adding together 49 g of $H_3BO_3$ and 117 g of $H_3PO_4$ (75% strength) in a kneader, evaporating off excess water and molding the product into 3-mm extrudates. These extrudates are dried at 110° C. and calcined at 350° C. Catalyst D contains 9.24% by weight of B and 29.5% by weight of P.

Catalyst E
Catalyst E is a precipitated aluminum phosphate prepared by precipitation from $Al(NO_3)_3$ and $H_3PO_4$ solution with $NH_3$ at pH 6-7. After filtration the precipitate is dried at 110° C. and calcined at 500° C. Catalyst C contains 22.7% by weight of Al and 25.3% by weight of P.

Catalyst F
Catalyst F consists of pyrogenic $TiO_2$ molded in the presence of a molding aid into 2-mm extrudates, dried at 110° C. and calcined at 500° C./16 h. The extrudates are treated with 15% strength HCl (weight ratio=1:10) at 80° C. for 1 hour, then washed until chloride-free, and dried at 110° C. and calcined at 600° C./1 h.

Catalyst G
Catalyst G consists of catalyst B impregnated with dilute phosphoric acid, dried at 130° C. and calcined at 540° C./2 h. The P content is 4.73% by weight.

Catalyst H
Catalyst H consists of commercial niobium oxide hydrate (61.2% by weight of Nb; 9.5% by weight of $H_2O$) molded with a molding aid into 2-mm extrudates, dried at 110° C. and calcined at 500° C./16 h.

Catalyst I
Catalyst I consists of catalyst B impregnated with dilute $NaH_2PO_4$ solution, dried at 110° C. and calcined at 500° C./14 h. It contains 6.2% by weight of Na and 7.7% by weight of P.

EXAMPLES 1 TO 3

A mixture of 2-methylimidazole, acetic acid and acetic anhydride (molar ratio=1:4:1) is vaporized and passed with a 6 l/h nitrogen steam at 450° C. over the catalyst under a WHSV of 4 $h^{-1}$.

The reaction product is condensed in a glass apparatus and analyzed by gas chromatography.

TABLE 1

| | | | | | Acetylation of 2-methylimidazole | | |
|---|---|---|---|---|---|---|---|
| | | | | | | GC analysis of output* | |
| Example | Catalyst | Run [h] | Temperature [°C.] | WHSV [$h^{-1}$] | 2-methyl imidazole [%] | N-acetyl-2-methyl-imidazole [%] | 4-acetyl-2-methyl-imidazole [%] |
| 1 | I | 6 | 450 | 4 | 19.5 | 0000 | 14.1 |
| 2 | C | 6 | 450 | 4 | 16.9 | 8.4 | 15.5 |
| 3 | D | 6 | 450 | 4 | 14.3 | 8.4 | 19.3 |

*output collected over 2 h following a run of 6 h.

EXAMPLES 4 TO 10

A mixture of imidazole, acetic acid and acetic anhydride (molar ratio=1:4:1) is vaporized and passed with a 6 l/h nitrogen stream at 450° C. over the catalyst under a WHSV of 3 $h^{-1}$.

The reaction product is condensed in a glass apparatus and analyzed by gas chromatography.

TABLE 2

| | | | | | Acetylation of imidazole | | |
|---|---|---|---|---|---|---|---|
| | | | | | | GC analysis of output* | |
| Example | Catalyst | Run [h] | Temperature [°C.] | WHSV [$h^{-1}$] | Imidazole [%] | N-acetyl-imidazole [%] | c-acetyl-imidazole [%] |
| 4 | B | 6 | 450 | 3 | 3.6 | 31.7 | 1.3 |
| 5 | E | 6 | 450 | 3 | 15.8 | 12.8 | 3.1 |
| 6 | C | 6 | 450 | 3 | 22.4 | 6.2 | 2.0 |
| 7 | F | 6 | 450 | 3 | 25.7 | 0.2 | 1.4 |
| 8 | A | 6 | 450 | 3 | 19.0 | 3.8 | 3.0 |
| 9 | G | 6 | 450 | 2 | 6.2 | 15.0 | 2.0 |
| 10 | H | 6 | 450 | 3 | 12.2 | 9.7 | 1.2 |

*averaged over 6 h runs.

EXAMPLE 11

The reaction is carried out in a 1-liter fluidized bed reactor in the gas phase. The temperature is 400° C. 60 g/h of a mixture of 2-methylimidazole and acetic anhydride (1:1.3 moles) are added, and 150 l/h of nitrogen are passed in as fluidizing gas. The reactor has been packed with 300 ml of catalyst in fluidizable form.

The catalyst used is commercial $SiO_2$ in fluidizable form.

Analysis of the reactor output indicates a 2-methylmidazole coversion of 87% and selectivity of 75% for 4-acetyl-2-methylimidazole.

We claim:

1. A process for preparing an acylated imidazole of the formula I

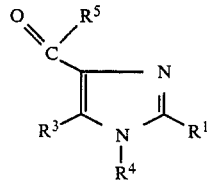 (I)

where $R^1$, and $R^3$ are each H, alkyl of from 1 to 12 carbon atoms, alkenyl of from 1 to 12 carbon atoms, aryl, aralkyl or alkylaryl, $R^4$ is H, alkyl of from 1, to 12 carbon atoms, alkenyl of from 1 to 12 carbon atoms, aryl, aralkyl or alkylaryl, and $R^5$ is alkyl of from 1 to 12 carbon atoms, alkenyl of from 1 to 12 carbon atoms, aryl, aralkyl, alkylaryl or carboxyl, which comprises reacting an imidazole of the formula II

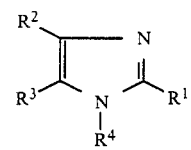 (II)

where $R^1$ $R^2$ and $R^3$ are each alkyl of from 1 to 12 carbon atoms, alkenyl of from 1 to 12 carbon atoms, aryl, aralkyl or alkylaryl, at least one of the radicals $R^1$, $R^2$ and $R^3$ being hydrogen, and $R^4$ is H, alkyl of from 1 to 12 carbon atoms, alkenyl of from, 1 to 12 carbon atoms, aryl, aralkyl or alkylaryl, with an acylating agent of the formula (III)

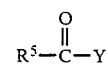 (III)

where $R^5$ is as defined above and Y is halide, alkoxy, acyloxy or hydroxyl, in the presence of an acidic metal oxide or a phosphate in the gas phase.

2. A process as claimed in claim 1, wherein the catalyst used is an oxide of the second, third or fourth main group or the third, fourth, fifth or sixth subgroup or a mixture thereof.

3. A process as claimed in claim 1, wherein the catalyst used has been treated with a phosphorus-containing substance.

4. A process as claimed in claim 1, wherein the catalyst used has been treated with a mineral acid.

* * * * *